(12) United States Patent
Brown et al.

(10) Patent No.: US 7,528,943 B2
(45) Date of Patent: May 5, 2009

(54) METHOD AND APPARATUS FOR SIMULTANEOUS HIGH-SPEED ACQUISITION OF MULTIPLE IMAGES

(75) Inventors: David L. Brown, Sunnyvale, CA (US); Yung-Ho Chuang, Cupertino, CA (US)

(73) Assignee: KLA-Tencor Technologies Corporation, Milpitas, CA (US)

( * ) Notice: Subject to any disclaimer, the term of this patent is extended or adjusted under 35 U.S.C. 154(b) by 198 days.

(21) Appl. No.: 11/318,715

(22) Filed: Dec. 27, 2005

(65) Prior Publication Data

US 2007/0146693 A1    Jun. 28, 2007

(51) Int. Cl.
*G01N 21/00* (2006.01)
(52) U.S. Cl. .................................. 356/237.4; 356/237.2
(58) Field of Classification Search ........................ None
See application file for complete search history.

(56) References Cited

U.S. PATENT DOCUMENTS

| | | | | |
|---|---|---|---|---|
| 5,760,899 | A * | 6/1998 | Eismann | 356/326 |
| 6,711,283 | B1 * | 3/2004 | Soenksen | 382/133 |
| 7,126,699 | B1 * | 10/2006 | Wihl et al. | 356/625 |

* cited by examiner

*Primary Examiner*—Michael P Stafira
(74) *Attorney, Agent, or Firm*—Smyrski Law Group, A P.C.

(57) ABSTRACT

A method and apparatus for simultaneous high-speed inspection and acquisition of multiple data channels is provided. The method and apparatus enables inspecting semiconductor wafers and reticles and comprises converting a single image region into two image sections, reorienting one image into a transposed configuration enabling simultaneous scanning of two inspected object locations with a single sensor, and controlling acquisition parameters for a second image by using information collected from a first image in a feedback arrangement. The design provides a dual-linear or time-delay-integration sensor operating in a split readout configuration mode to simultaneously provide data from two regions of the sensor using two sets of readout circuitry.

28 Claims, 11 Drawing Sheets

METHOD AND APPARATUS FOR SIMULTANEOUS HIGH-SPEED ACQUISITION OF MULTIPLE IMAGES

BACKGROUND OF THE INVENTION

1. Field of the Invention

The present invention relates generally to the field of automated high-speed imaging systems, and more specifically to electro-optical inspection and metrology systems for semiconductor wafers and reticles.

2. Description of the Related Art

Semiconductor wafer and reticle inspection tools are constantly being improved to meet the growing challenges of inspecting smaller and smaller features. Rapid advancements in new device structures, materials, associated lithography techniques, and reticle enhancement strategies for developing circuits are dramatically increasing circuit complexity. Increased complexity resulting from smaller features in conjunction with the advancement in manufacturing materials and techniques impose increased demands and additional requirements on the semiconductor silicon wafer inspection process. In particular, the materials and techniques produce new defect types and noise sources, resulting in a dramatic rise in critical defects along with greater difficulty of detection.

To meet these demands, today's industrial inspection and metrology imaging systems enable the collection of more than one channel of information for both static imaging and high-speed scanning defect detection systems. The term "channel" or the like used herein means an imaging mode, including but not limited to: bright field and dark field imaging, large-signal/small-signal readout, multi-spectral imaging, transmitted/reflected simultaneous imaging, and broadband/narrow band optical imaging modes. Multiple mode inspection is becoming an industry wide necessity to ensure optimal detection of the broadest range of defect types.

As a result, manufacturers now produce inspection systems capable of supporting multiple configurations to affect a wide variety of imaging collection modes and are optimizing components for specific inspection applications, thus providing system solutions that collect more than one channel of information. For example, a wafer surface inspection system may use a dark field imaging mode to detect highly scattering particles such as dust on a smooth and uniform surface and a bright-field imaging mode to identify stains or other surface contamination.

Traditionally, wafer inspection systems have employed sensors such as time-delay-integration (TDI) sensors to inspect an object using die-to-die or die-to-database inspection techniques. Collecting more than one channel of information during the inspection process can be technically difficult, but particularly can be time consuming. Conducting multiple inspections, in conjunction with performing certain measurements, significantly increases the total required inspection time and expense.

Thus it would be advantageous to offer an inspection architecture and design employing a sensing device or devices, wherein the inspection design provides robust and reliable image collection, capable of use with multiple imaging modes, and overcomes the drawbacks associated with previous systems used to perform multiple mode inspections.

SUMMARY OF THE INVENTION

According to a first aspect of the present design, there is provided a sensor configured to receive light energy for purposes of inspecting a specimen. The sensor comprises a first sensing region configured to receive a first channel of image data from the specimen and a second sensing region configured to receive a second channel of image data from the specimen. The sensor further comprises first readout circuitry connected to the first region configured to read the first channel of image data from the sensor and second readout circuitry connected to the second region configured to read the second channel of image data from the sensor simultaneous with reading the first channel of image data from the sensor.

According to a second aspect of the present design, there is provided a system for performing a simultaneous dual channel inspection of a specimen. The system comprises at least one illuminator configured to provide light energy to the specimen, orientation optics configured to receive two channels of light energy from the specimen and reorient one channel of light energy, thereby configured to provide a reoriented channel of light energy and a nonreoriented channel of light energy, and a sensor configured to receive and simultaneously process the reoriented channel of light energy and the nonreoriented channel of light energy in a compact fashion.

These and other advantages of the present invention will become apparent to those skilled in the art from the following detailed description of the invention and the accompanying drawings.

DESCRIPTION OF THE DRAWINGS

The present invention is illustrated by way of example, and not by way of limitation, in the figures of the accompanying drawings in which.

DETAILED DESCRIPTION OF THE INVENTION

The present design employs a TDI sensor to perform scanning of a specimen such as a semiconductor wafer. The TDI sensor has the ability to receive data transmitted in two separate configurations, such as brightfield and darkfield data, and pass the two sets of data from both sides of the TDI sensor to processing hardware and software. Former TDI bidirectional sensors have employed only one side of the TDI sensor and one set of associated hardware on a pass in one direction, and the other side of the sensor and a second set of associated hardware when a pass is made in the other direction. The present design uses both sides of the sensor and two sets of associated hardware simultaneously to scan in two modes in one pass. This dual channel implementation is realized using a novel arrangement of lenses, reflective surfaces, relays, and other components to provide two channels of data for a single surface to a TDI sensor.

Overall System Construction

The present design description provides a method and apparatus for automated high-speed imaging. While the design may be used in various environments and applications, it will be discussed herein with a particular emphasis on a semiconductor wafer or reticle inspection environment. For example, one embodiment of the present design is a semiconductor wafer inspection system or method suitable for inspecting masks, reticles, and wafer surfaces used in the semiconductor industry. The present design may employ one or more illumination sources (i.e. image modes) to produce one or more images of the specimen or wafer being inspected.

Figure 1A:
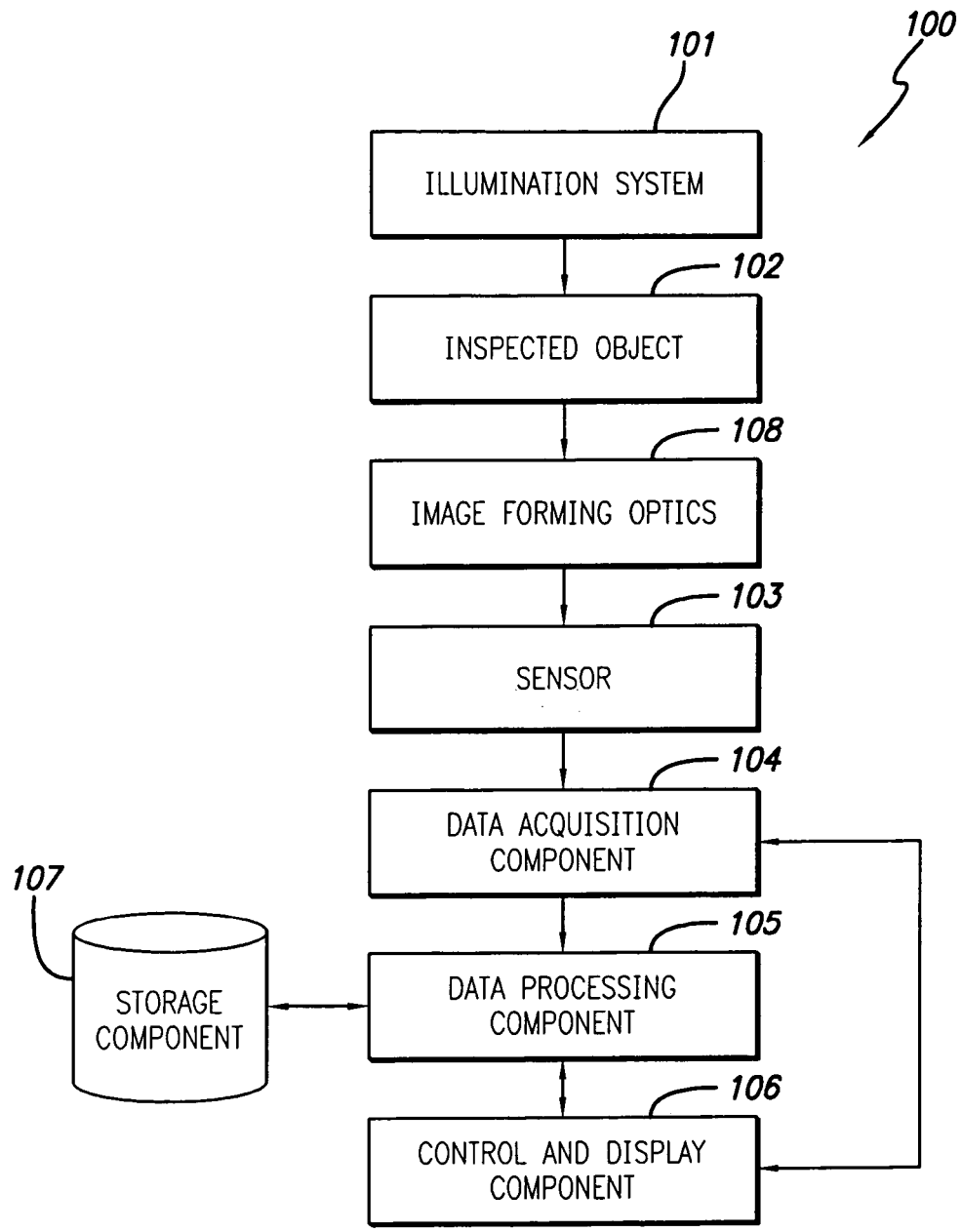
FIG. 1A is a block diagram illustrating the present design components and interfaces of an inspection system.

FIG. 1A illustrates the present design components and interfaces of an inspection system 100, where the particular embodiment illustrated in FIG. 1A contemplates inspection of a semiconductor wafer, photomask or reticle. The inspection system 100 in this embodiment includes an illumination system 101, an inspected object 102, and a sensor 103 for generating image data responses representing multiple imaging modes. Illumination system 101 may comprise one or more illumination sources, where if multiple illumination sources are provided, each source emits light energy with different spectral and coherence properties for projection onto an inspected object 102.

Inspected object 102 reflects, transmits, or scatters light energy and image forming optics 108 transport the light energy onto a sensor 103. Sensor 103 simultaneously generates output for two separate image data responses or signals of inspected object 102. The present design may transport the output signals generated by sensor 103 to a data acquisition component 104 to capture the sensor output. Data acquisition component 104 may then transport the acquired signals to a data processing component 105 for real-time image analysis. Additionally, data processing component 105 may store the signal output in storage component 107 for recording image data sufficient for post data collection analysis. Moreover, the data storage component may store inspection and metrology information for use in die-to-database analysis, a procedure generally known to those skilled in the art. A control and display component 106 may provide user interaction and inspection system status sufficient recording image signals generated by sensor 103. Furthermore, control and display component 106 may provide manual or automated real-time feedback control for acquisition, analysis, data processing, storage and reporting of obtained inspection and metrology results.

While depicted as multiple elements, data acquisition component 104, data processing component 105, and control and display component 106 may alternatively be comprised of a single computer device or a set of distributed computer devices that fulfill the functionality and purposes of the acquisition, processing, control and display components, described in further detail herein.

Figure 1B:
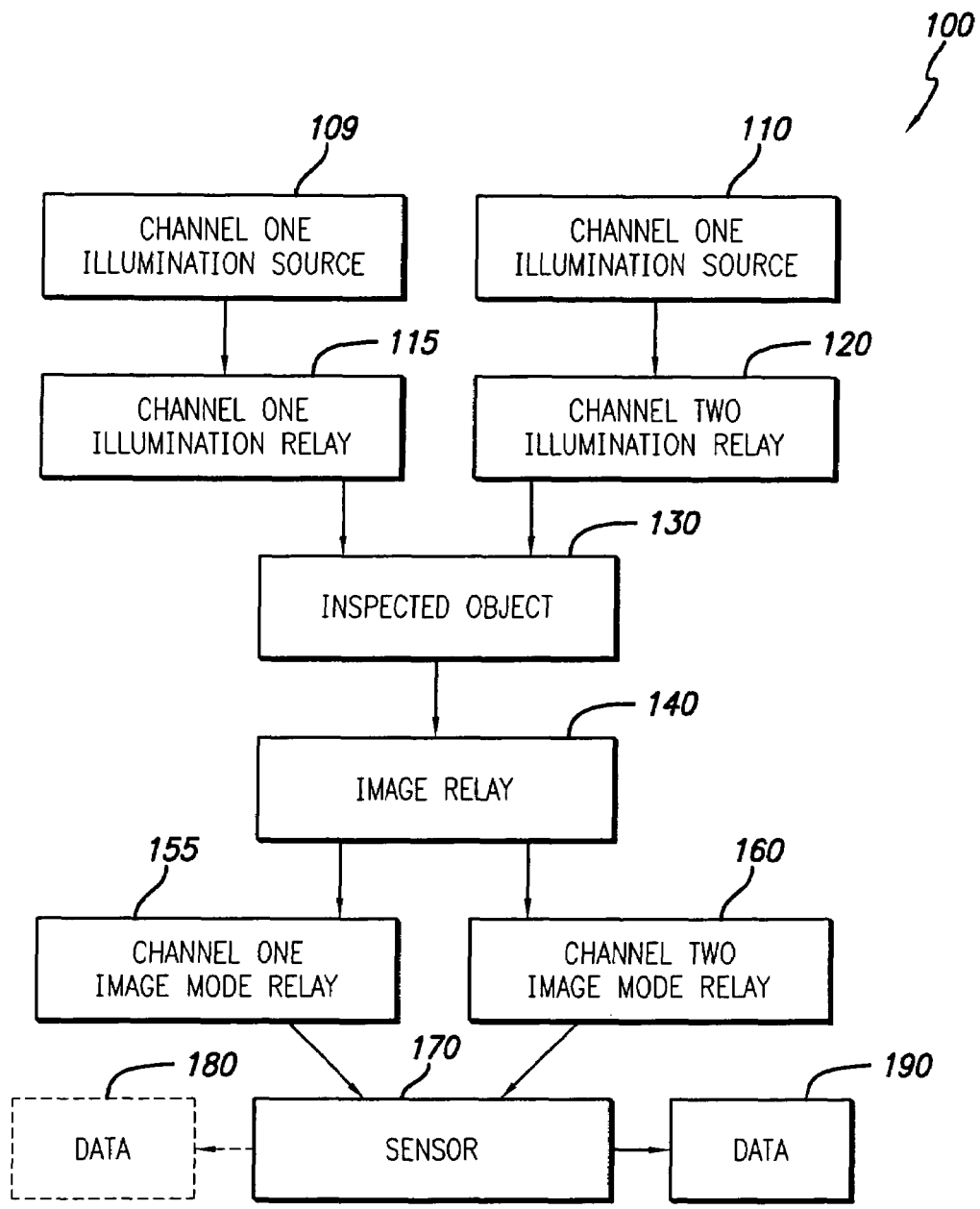
FIG. 1B is a general flow diagram of a representative inspection system to illustrate possible implementations for all aspects of the present design.

A general representation of an inspection system 100 illustrating the information flow and major system components for simultaneously collecting multiple images on one sensor in accordance with the present design is presented in FIG. 1B. The present design may include an image forming arrangement, sensor, and a data acquisition component configured to support one or more light sources and illumination relay components constructed with at least one imaging lens. The design further includes a sensor.

The present design generally provides simultaneous support for two light source paths through the inspection system 100. FIG. 1B provides the basis for multiple possible implementations featuring different aspects of the present design. From FIG. 1B, a channel one illumination source 109 emits light energy or flux (e.g. dark field channel) and may direct light energy toward illumination relay 115. While the present design may allow various illumination modes, the example of FIG. 1 will be discussed herein where the channel one illumination source provides dark field imaging. The channel one illumination relay 115 may comprise one or more reflective surfaces, a beam splitter, a reflector, a polarization lens, and/or an illumination and imaging lens relay arrangement. A channel two illumination source 110 emits light energy or flux and may direct the light energy toward illumination relay 120. In the present example, the channel two illumination source provides bright field imaging. The channel two illumination relay 120 may comprise one or more reflective surfaces, a beam splitter, a reflector, a polarization lens, and/or an illumination and imaging lens relay arrangement.

Again, illumination sources or imaging modes may include, but are not limited to, bright field and dark field imaging, large-signal/small-signal readout, multi-spectral imaging, transmitted/reflected simultaneous imaging, and broadband/narrow band optical imaging modes, and any combinations thereof. Also, some components may be shared between illumination paths.

The channel one illumination relay 115 may collect light energy emitted from the channel one illumination source and may project the light energy or flux onto the inspected object 130. In addition, the channel two illumination relay 120 may collect light energy emitted from the channel two illumination source and may simultaneously project the light energy or flux onto the inspected object 130 in combination with channel one illumination.

In this configuration, the present design affords simultaneous light exposure of the inspected object 130 using two imaging modes. The present design may collect the light energy that is transmitted, reflected, or scattered from inspected object 130 (i.e. specimen under inspection) at image relay 140. Image relay 140 collects the light energy and may split or separate the light energy into two separate channels or imaging modes. Image relay 140 may transfer or pass the split energy to one or more imaging mode relays. Image relay 140 may transfer dark field light energy to a channel one image mode relay 155. In a similar manner, image relay 140 may transfer bright field light energy to a channel two image mode relay 160.

The channel one image mode relay 155 receives reflected dark field light energy from image relay 140 and transfers or projects the reflected dark field light energy onto sensor 170. Image relay 140 and image mode relays 155 and 160 may comprise any combination of mirror(s), beam splitter(s), reflector(s), polarization lens(es), and/or lens relays or other relay components Sensor 170 may include, but not limited to a dual linear sensor, time-delay-integration (TDI) sensor, or any other collection device suitable for fulfilling the purposes of sensor 170. Sensor 170 simultaneously outputs detected information via a plurality of readout circuits (not shown in FIG. 1) as separate image data. In this general representation, the present design provides the dark field response as image data at point 180 and the bright field response as image data at point 190.

The representation in FIG. 1 illustrates a generalized representation of a system, which may employ the present design. The functionality critical to the present design includes that of providing light energy for one or more imaging modes and transporting the resulting information as two separate images through the system. Moreover, the present design orchestrates independent image data resulting from the two illumination sources in a manner such that, in the present example, the dark field and bright field images simultaneously strike sensor 170.

Sensor Configuration

The present design employs a TDI sensor having the ability to receive data in two separate channels, such as brightfield and darkfield channels, and pass the data from both sides of the TDI sensor to processing hardware and software. Former TDI sensors have employed one side of the sensor and one set of associated hardware on a pass in one direction and the other side of the sensor and a second set of associated hardware when a pass is made in the other direction. The present design uses both sides of the sensor and two sets of associated hardware to scan in two modes in one pass.

In this configuration, a single sensor may provide simultaneous readouts in response to two illumination sources and may generate a separate output data stream for each image incident on sensor 170. The present design affords analysis improvements, on the inspected object 130, without requiring additional time to conduct two or more inspections.

Figure 2:
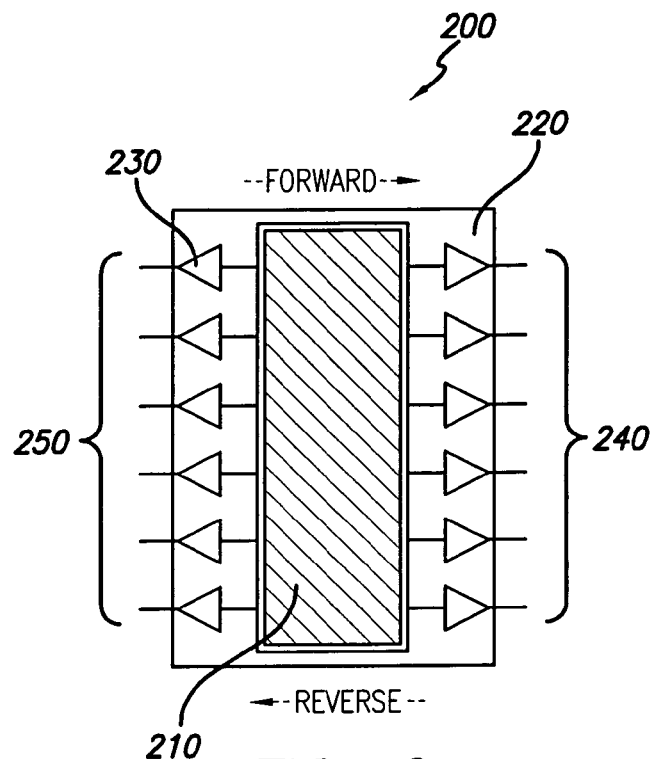
FIG. 2 is a schematic representation of a conventional bidirectional time-delay-integration (TDI) sensor.

A schematic diagram of a conventional bidirectional TDI sensor 200 for acquiring an image, shown in FIG. 2, illustrates the on-chip readout circuitry along each side of bidirectional TDI sensor 200. Bidirectional TDI sensor 200 may provide signal output from a unidirectional scan in either a forward or a reverse scanning direction as shown in FIG. 2. In the forward scanning direction, bidirectional TDI sensor 200 receives light energy reflected off the inspected object 130 and forms an image 210 representing the received energy. Scanning in the forward direction produces signal output at a plurality of individual amplifier circuits 220. The data collected from the entire image sensor region 210 produced from scanning in the forward direction emerges as output at forward readout circuits 240.

Forward readout circuits 240 may transmit the output to a data acquisition system (not shown in FIG. 2) for capturing the signals produced by bidirectional TDI sensor 200. Furthermore, scanning in the reverse direction produces signal output at a plurality of individual amplifier circuits 230. The data collected from the entire image sensor region 210 produced from scanning in the reverse direction emerges as output at reverse readout circuits 250. Reverse readout circuits 250 may transmit the output to a data acquisition system (not shown in FIG. 2) for capturing the signals produced by bidirectional TDI sensor 200. In other words, only one side of TDI sensor 200 is read out at any one time. The signals collected by the data acquisition system may be compared with other stored or processed image data or with known design information in order to ascertain the quality of the specimen or wafer.

Figure 3:
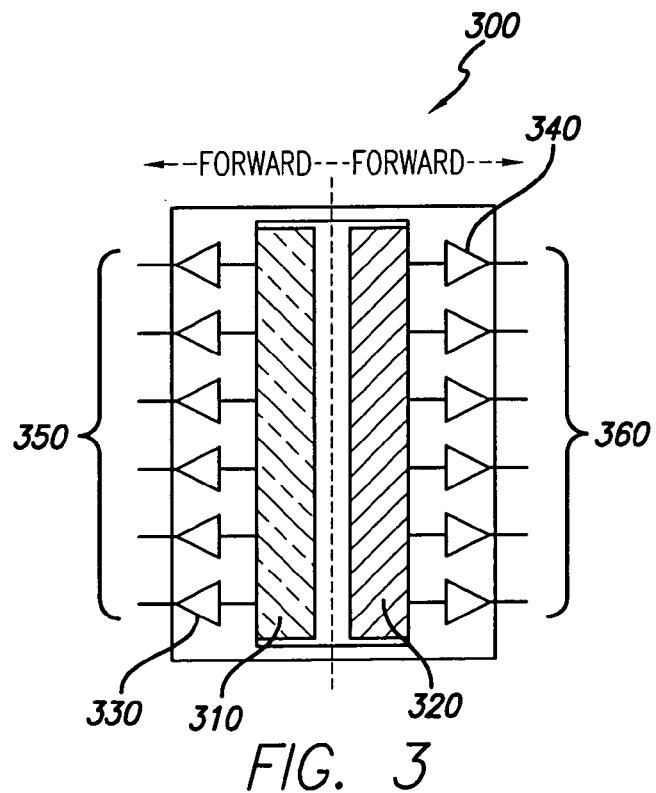
FIG. 3 is a schematic representation of a bidirectional TDI sensor configured to operate in a split readout mode in accordance with the present design.

A schematic diagram of a split readout TDI sensor 300 configured in a split readout operating mode, shown in FIG. 3, illustrates the on-chip readout circuitry continuously active along each side of the sensor. Split readout TDI sensor 300 may acquire two separate continuous image streams simultaneously by providing signal outputs from scanning the inspected object 130 in a single direction (e.g. forward). Split readout TDI sensor 300 receives, in this example, dark field light energy reflected off the inspected object 130 and forms image 310 representing the received dark field energy. A single scan in the forward direction produces output for the dark field response via a first plurality of individual amplifier circuits 330. The data from the entire image sensing region 310 emerges as output at image one "forward" readout lines 350. Image one forward readout lines 350 may transmit the output to a data acquisition system for capturing the signals produced by split readout TDI sensor 300.

Furthermore, along with the forward scan used to produce image one, device operation is generally configured to simultaneously scan the same or, optionally, a different region of the specimen or wafer and produce a second independent image on split readout TDI sensor 300. In one embodiment a mirror arrangement, capable of splitting two images at an intermediate field plane and reorienting one image, may be employed to obtain light energy representing the second image.

Figure 4B:
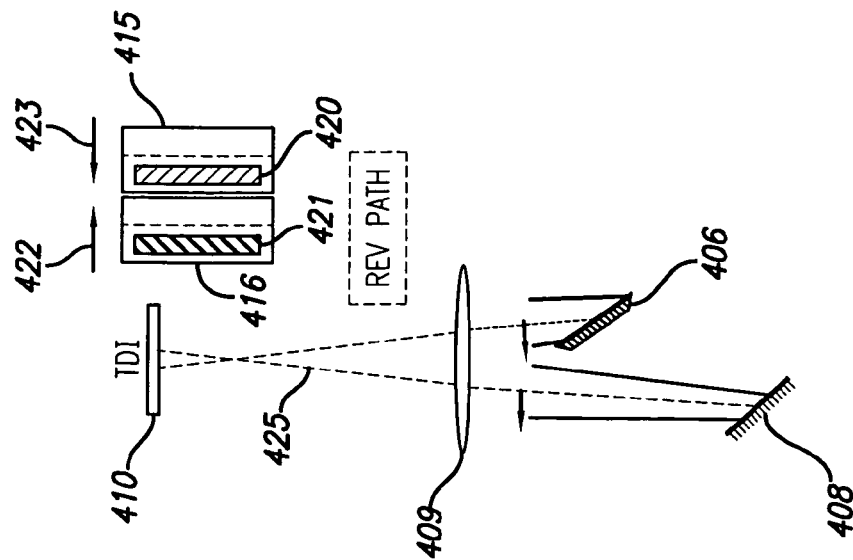
FIG. 4B is a general representation of inspection system optics employing the present design operating in a reverse direction.

A mirror/reflective surface arrangement enables collecting and transferring the resulting image composition information and projecting the second illumination mode onto and subsequently out of split mode TDI sensor 300. The sections that follow provide specific details encompassing the present design optical arrangement for collecting information from a single scan in either direction and yielding output data incident on a sensor in two opposite directions and are shown in FIG. 4 and FIG. 5.

The split readout operating mode enables TDI sensor 300 to receive, in this example, a second channel of bright field light energy that forms image two at region 320 based on the received bright field energy. Scanning forward produces signal output of the bright field response at a plurality of individual amplifier circuits 340. The data produced from the entire image sensor region 320 emerges as output at image two forward readout circuits 360. Image two forward readout circuits 360 may transmit the output to a data acquisition system for capturing the signals produced by TDI sensor 300. The signals collected by the data acquisition system may be compared with other stored or processed image data or with know design information in order to conduct the inspection process. The TDI sensor split mode operation of the present design enables high-speed acquisition of two images and high sensitivity from a single scan of the inspected object 130.

The split readout TDI sensor 300 of FIG. 3 can therefore be employed to scan two separate images or two identical images wherein if the scan of images is properly configured or oriented, data may be collected by both sides or regions 310 and 320 of sensor 300 and may continuously feed data to image one forward readout lines 350 and image two readout lines 360 via first plurality of individual amplifier circuits 330 and second plurality of individual amplifier circuits 340, respectively. Thus as opposed to the previous construction of FIG. 2, the construction of FIG. 3 can employ all components (amplifier circuits and readout lines) associated with the split readout TDI sensor 300 at one time, thereby potentially increasing scan throughput and improving overall inspection performance.

FIG. 4 illustrates one embodiment of the present design where two regions of the specimen or wafer at 401 are imaged onto a sensor 410. The two regions may comprise a single region of the specimen or wafer being imaged at different times and in a different manner, such as using a different wavelength of light energy. The region or regions being inspected, for purposes of illustrating the orientation of the area(s) imaged at different points in the arrangement, are shown as arrows. Of particular note is that the second image, shown as the light headed arrow, is separated from the first image, shown as the dark headed arrow, at a point on reflective surface 404 and reoriented for transmission onto the sensor 410. As described above, an illumination system (not shown) may be, for example, a lamp based system where light is injected into the system using a beamsplitter known in the art of microscope design.

A top view of the image being inspected in this embodiment is shown by specimen field 414, comprising first region 420 and second region 421. Direction of scan is indicated by arrow 411. The light energy from the illumination system is incident at region 420 and may be reflected or scattered and collected by lens 402 and may be focused by lens 403. For the second region 421 the illumination could have different spectral or polarization properties or, in the case of a light transmitting object such as a reticle, light may be transmitted through the specimen. The arrangement allows both image regions to be collected simultaneously.

The imaging system object field 414 is therefore located at position 401. The imaging system splits the specimen field 414 into a first partial field 415 and a second partial field 416 and relays them through a focusing lens 409 in this embodiment to the image location on sensor 410. Each partial field contains only one region, 420 or 421, as the reflective surface 404 separates the object field 414 into two regions. The two image partial fields 415 and 416 are shown without overlap for clarity but the positions of regions 420 and 421 may be adjusted using reflective surface 406 and reflective surface 408 to place them in close proximity at the image plane of sensor 410.

Figure 4A:
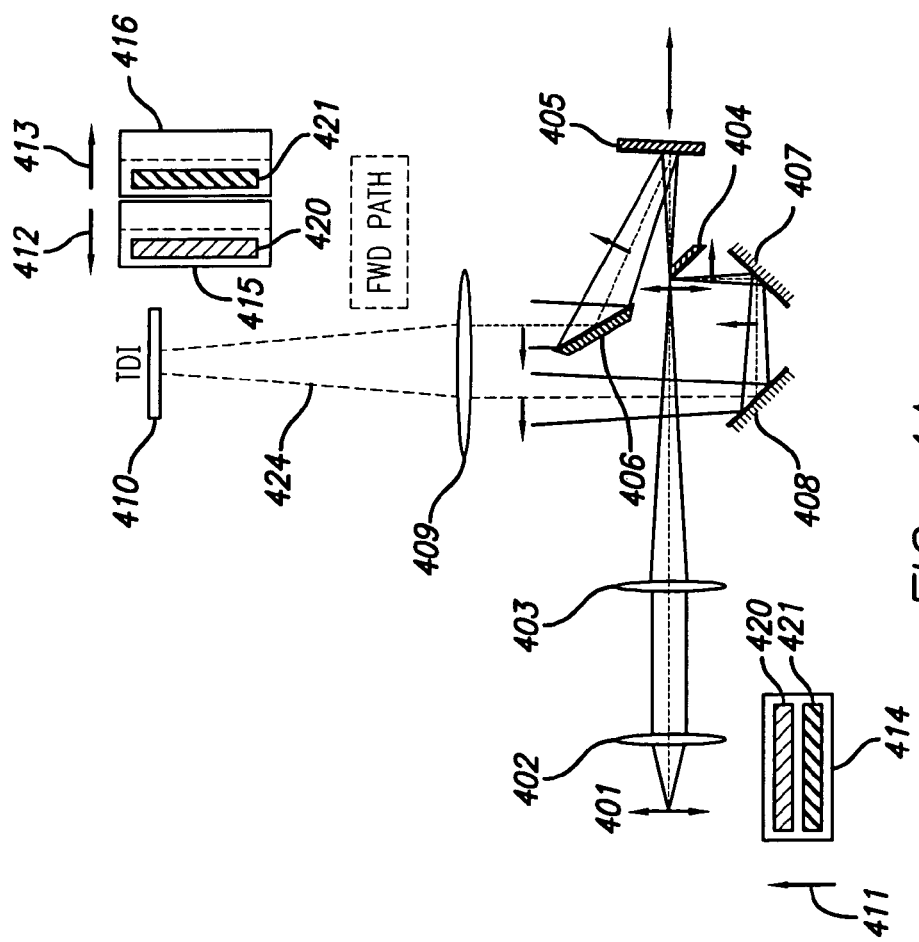
FIG. 4A is a general representation of inspection system optics employing the present design operating in a forward direction.
Figure 5:
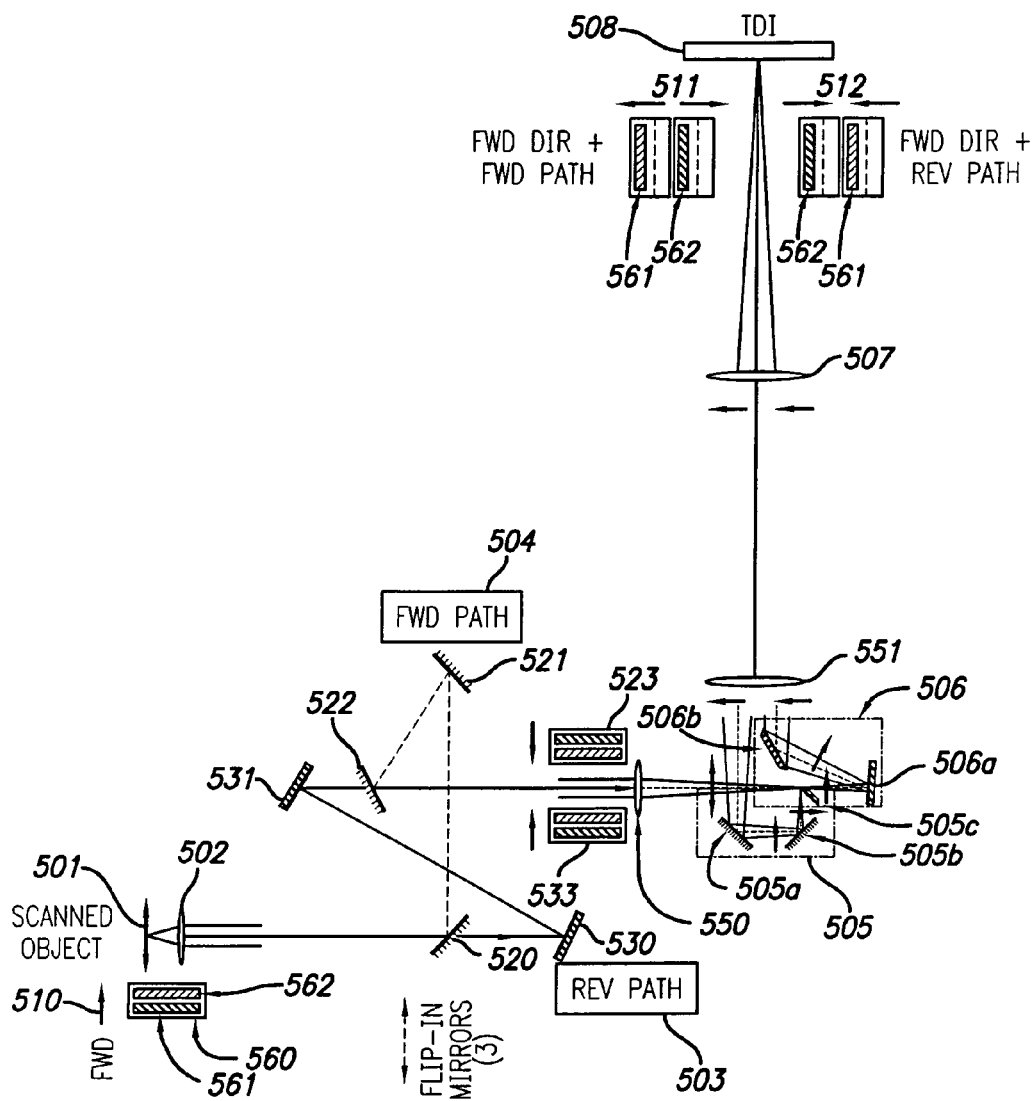
FIG. 5 is a general representation of inspection system optics employing the present design and capable of operating in either direction.

If the inspected object field 414 moves according to direction indicated by 411, the forward path case of FIG. 4A illustrates in the upper part of the Figure the scan direction of the two regions at the sensor 410. In this case, partial field 415 moves according to direction 412 and partial region 416 moves according to direction 413. Ray paths 424 indicate the approximate alignment of the two regions 420 and 421 on the sensor 410.

The reverse path case of FIG. 4B also shows the scan direction of the two regions at the sensor 410. In this reverse path case, the partial field 415 moves according to direction 423 and partial region 416 moves according to direction 422. Ray paths 425 indicate the approximate alignment of the two regions 420 and 421 on the sensor 410. In this manner, the direction of the scanned regions can be controlled relative to the image projected onto the sensor. This reverse path case and the orientation of images on the sensor can be produced by changing the angles or positions of reflective surfaces 406 and 408 as shown in FIG. 4B.

In scanning mode operation, using the reverse path, the specimen location in the first image region 420 will move during the scan and will be imaged in the second image region 421 at a later time. In this way the two image regions can inspect or scan the same object locations. After adjusting for the data collection time delay between the two regions this design can provide for a comparison of a single location on the object using two imaging modes.

FIG. 5 represents an embodiment similar to FIGS. 4A and 4B but showing an alternative method for changing the scan direction and orienting the images on the sensor. The specimen located at 501 is shown as two differently oriented arrow heads and is imaged by lens 502 and additional relay lenses and reflective surfaces to a sensor 508 at the image location. Relay locations 505 and 506, comprising multiple reflective surfaces 505a, 505b, 505c and 506a and 506b, split and orient the image regions for receipt by sensor 508. In one case, labeled reverse path, reflective surfaces 530 and 531 are used in the optical relay. In normal operation, i.e. in the reverse path, light energy is incident on the specimen and is received at lens or optical element 502. Light energy then passes, as shown by the solid line(s), to reflective surface 530, reflective surface 531, lens 550, and relay locations 505 and 506. Out of relay locations 505 and 506 the light energy passes to lens element 551 and focusing lens element 507 in the orientation shown and onto sensor 508. The reflective surfaces 520, 522, and 521 are thus not in place and do not receive, reflect, or transmit light energy in the forward path shown.

In order to change scan direction, three additional reflective surfaces 520, 521, and 522, are positioned in the system. These reflective surfaces may be fixed on one mount and moved in place as one unit to allow a convenient mechanical selection between scan directions. When these three reflective surfaces are in use, the forward path is in operation, and the two original reflective surfaces 530 and 531 are not used. Several optical design alternatives may be employed for this reverse-forward light energy selection. However, for optimal performance the optical path lengths from reflective surface 520 to reflective surface 522 should be the same for both configurations and not change when the image scan direction is changed. In other words, the dotted line distance in FIG. 5 from reflective surface 520 to reflective surface 521 to reflective surface 522 in the forward path is the same as the optical distance along the solid line (reverse path) from the position of reflective surface 520 to reflective surface 530, reflective surface 531, and the point of reflective surface 522. Identical optical path lengths can reduce or eliminate the need to compensate for relative changes in image quality between paths, such as focus and/or magnification. No further changes in image alignment are generally needed, and thus no image quality differences are encountered in the present design due to lens aberrations when the scan direction changes from forward to reverse in the arrangement of FIG. 5.

Again, the specimen surface 560 is shown with two scan regions 561 and 562 that are provided to the sensor 508 depending on the path employed. When reflective surfaces 520, 521, and 522 are positioned for use (forward path), the scan direction shown as scan direction 510 maps to scan direction 511 at the sensor 508. When reflective surfaces 530 and 531 are positioned for use (reverse path), scan direction 510 maps to scan directions 512 at the sensor 508. Intermediate orientations are shown at point 523 for the forward path and 533 for the reverse path.

Thus as shown in FIGS. 4A, 4B, and 5, the orientation of components within the optical arrangement, typically comprising lenses, beamsplitters, and/or reflective surfaces, can cause the resultant light energy imposed on the surface of sensor 410 or sensor 508 to progress in directions differing from the scan direction. So as shown in FIG. 5, a forward scan 510 of a specimen surface 560 having region 561 and region 562 yields region 561 being scanned in direction 511, i.e. to the left, and region 561 scanned in direction 511, i.e. to the right, at the sensor 508. Data thus progresses in an outward fashion at the TDI sensor for both images of the specimen surface being scanned for forward or reverse specimen scan directions.

Various Sensor Designs

Figure 6:
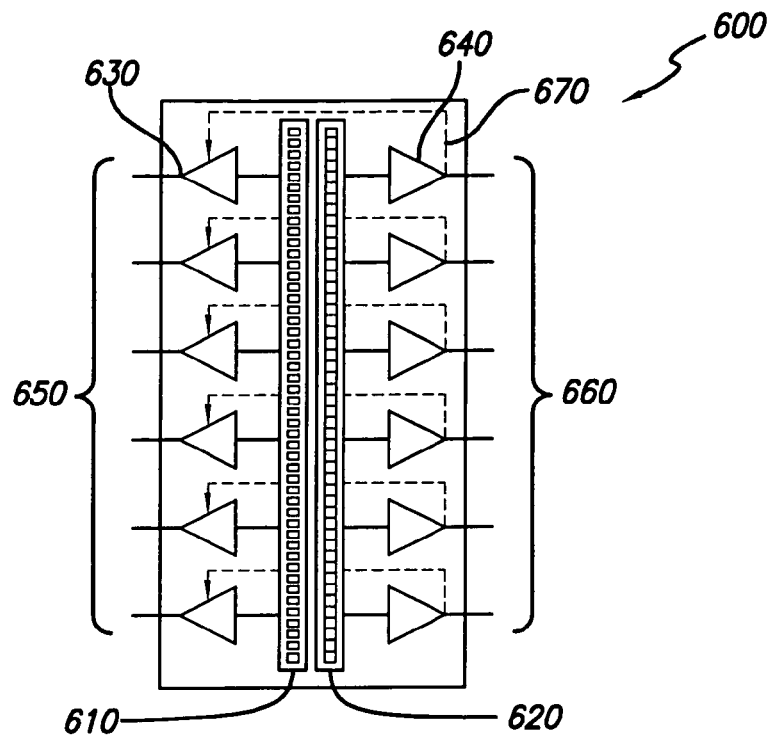
FIG. 6 is a schematic representation of a dual linear sensor configured for acquiring two separate scan images simultaneously in accordance with the present design.

A schematic representation of a dual linear sensor 600 containing two integrated but spatially separated 1×N line sensor sub-arrays is shown in FIG. 6. FIG. 6 illustrates the on-chip readout circuitry along each side of the sensor. Dual linear sensor 600 may acquire two scanned images simultaneously and each sub-array may operate independent of the other. Furthermore, the present design may forward output or control signals generated from one side of dual linear sensor 600 for the purposes of controlling exposure and modifying output parameters on the second side of dual linear sensor 600. Each 1×N line sensor sub-array may collect image data one pixel wide. Collecting one pixel wide image data on at least one sub-array eliminates the image reorientation requirement and may mitigate other related acquisition and processing effects that could produce image blur. In this configuration, the dual linear sensor 600 may employ two sub-regions of the sensor to record scanned image data from inspected object 130. The sub-regions may scan the same location on inspected object 130 simultaneously using, but not limited to: different imaging modes, illumination sources, illumination levels, wavelengths, spectral ranges, polarizations, and/or other illumination characteristics.

Dual linear sensor 600 receives light energy from the inspected object 130 in the form of a one pixel wide image one 610 representing the received energy. The image one 610 data may produce signal output at one or a plurality of individual amplifier circuits 630. The data representing image one 610 emerges as output at line one readout circuits 650. Line one readout circuits 650 may transmit the output to a data acquisition system (not shown in FIG. 6) for capturing the signals produced by dual linear sensor 600.

Furthermore, the same scan that produces image one may also produce a second image data stream from dual linear sensor 600. The present design may obtain reflected energy representing a second image using the mirror arrangement previously described. The independent sub-regions may allow dual linear sensor 600 to receive light energy reflected off inspected object 130 and form a one pixel wide image two 620 based on the received energy. Scanning in this manner using this arrangement produces signal output at a plurality of individual amplifier circuits 640. The data representing the one pixel wide image two 620 produced emerges as output at line two readout circuits 660. Line two readout circuits 660 may transmit the output to a data acquisition system (not shown in FIG. 6) for capturing the signals produced by dual linear sensor 600. The signals collected by the data acquisition system may be compared with other stored images or with know design information in order to conduct the inspection process.

Moreover, the present design may introduce a time delay between the instant when the first sub-region scans a location on inspected object 130 and when the second sub-region scans the same inspected object 130 location. In this configuration, the output from the first sub-region may provide information to on-chip control logic, which in-turn may provide a mechanism for modifying the acquisition parameters employed by the second sub-region. For example, a control circuit 670 may provide the output signal produced by amplifier circuit 640 to amplifier circuit 630. The present design enables controlling line one readout circuits 650 by observing inspected object 130 properties, in the form of output signals produced by amplifier circuit 640, to modify exposure time, amplifier gain, or manipulate other acquisition parameters. For example, to eliminate saturation effects and effectively increase the acquisition system's dynamic range, the first sub-region measures the signal reflected from inspected object 130, and provides the resulting control signal for the exposure of the second sub-region.

Figure 7:
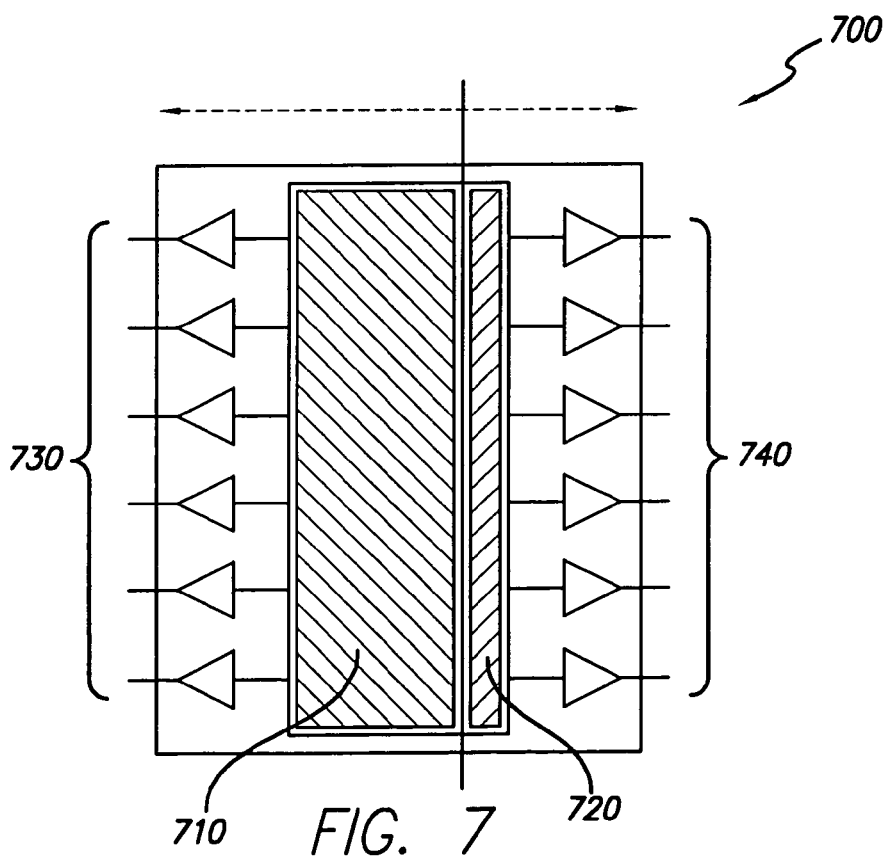
FIG. 7 is a schematic representation of a bidirectional TDI sensor configured to use different areas for each scan image region in accordance with the present design.

FIG. 7 illustrates a schematic representation of an M×N split readout TDI sensor 700 configured in a split readout operating mode, where the particular aspect illustrated in FIG. 7 contemplates a configuration employing a large sub-region on one side of bidirectional TDI sensor 700 and employing a smaller sub-region on the second side of split readout TDI sensor 700. Configuring different sized image sub-region areas allows for sensitivity and dynamic range optimization and may accommodate two illumination sources with differing properties (e.g. a higher-brightness and a lower-brightness illumination source). The high-sensitivity image channel 710 sub-region employs a large number of pixels for increased signal integration, while the large-signal image channel 720 sub-region may employ just a few or even a single line of pixels resulting in reduced signal integration and capable of detecting larger signals without saturation. Modifying the size of each image channel sub-region allows the present design to reliably measure very large signals and small signals from a region with improved dynamic range corresponding to the ratio of the number of integration stages.

The present design enables selecting the most appropriate output image data signals from only the first circuit 730 or only the second readout circuit 740, while ignoring the other output, or selecting both outputs and combining the image data signals to form a composite image. In one configuration, dark field energy may be transmitted to the larger sub-region 710 while bright field energy may be transmitted to the smaller sub-region 720. The ability to choose the appropriate integration ratios may allow optimum inspection with different imaging modes in a single inspection scan.

One example of selecting the appropriate integration ratio occurs where the imaging modes selected produce a significant difference in the image signal as found in dark field and bright field imaging when using a single illumination source. The dark field image mode may produce a lower signal for certain inspected object 130 patterns that do not scatter light energy efficiently. In this example, the high-sensitivity image channel 710 provides dark field imaging of the region to detect lower signals, while the low-sensitivity large signal image channel 720 provides bright field imaging of the inspected region.

A second example illustrating use of selecting the appropriate integration ratio may occur where the imaging modes selected produce a significant difference in the image signal as found in broadband spectrum and narrowband or multi-line spectrum imaging. The total signal available from the broadband spectrum may be significantly larger than for the narrowband or a line-filtered source. The present design may use the high-sensitivity image channel 710 for the narrowband-filtered source, affording the most efficient use of the available illumination reflecting off of the inspected object 130. If two different light sources are used for illumination, for example a lamp and a laser source are used together, the brightness of each source (i.e. light energy) may be quite different. To accommodate a difference in brightness, the high-sensitivity image channel 710 may collect reflected light produced from the lower light energy source and the low-sensitivity large-signal image channel 720 may collect reflected light produced from the higher brightness source.

Moreover, if different regions of inspected object 130 respond with widely differing reflected and scattered light levels when illuminated, selecting an appropriate TDI integration ratio may allow for highly optimized inspection of these different regions in a single scan. As noted above, such a construction may employ a TDI sensor 700 having two regions of different sizes (M×N), approximately similar sizes (M×M), lines (M×1, 1×N, or 1×1), or other arrangement, wherein use of different size configurations can improve dynamic range of TDI sensor 700 and offer sensitivity control by using regions having different numbers of integration stages or image widths.

Figure 8:
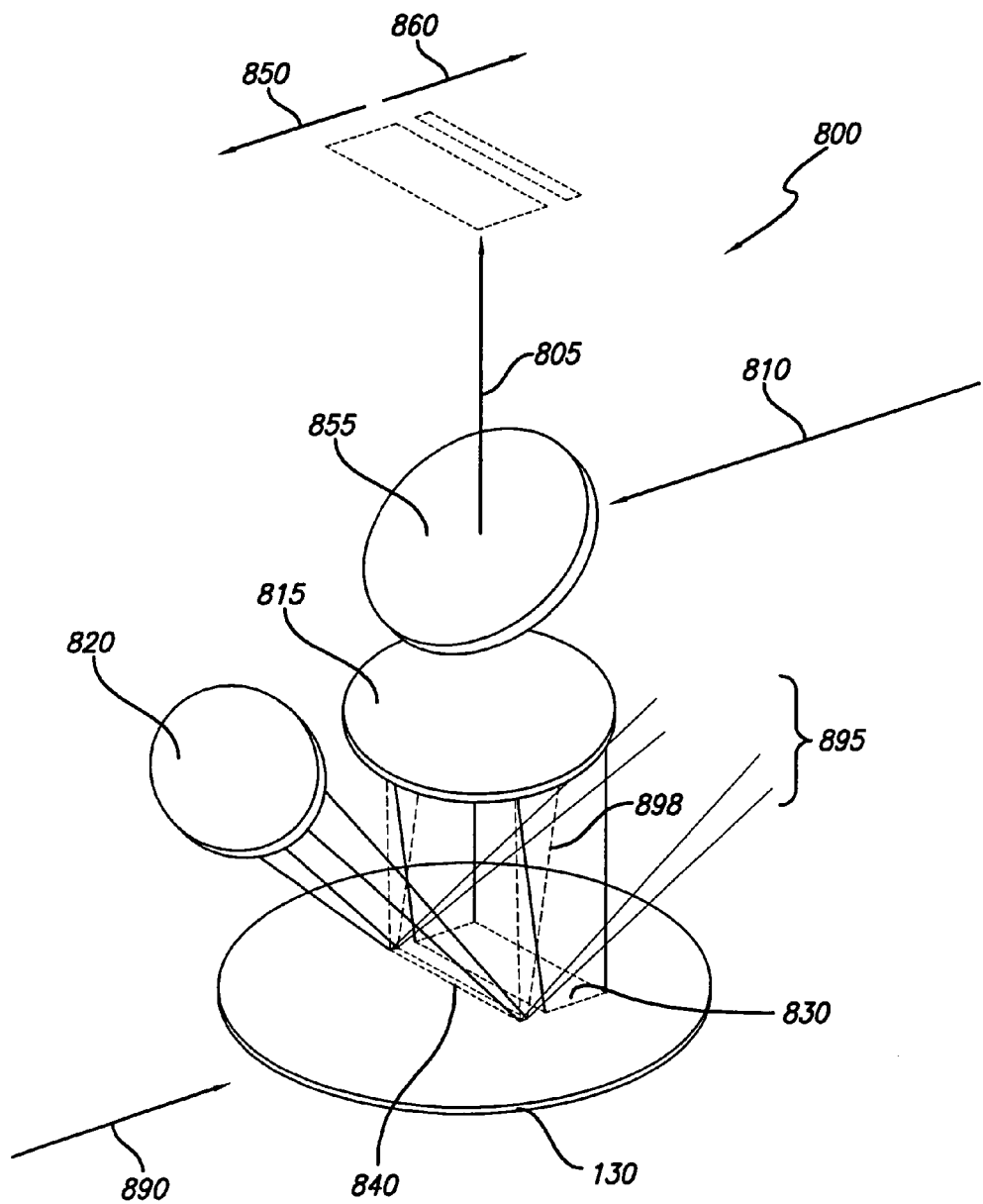
FIG. 8 is a general representation of an inspection system configured with two illumination sources and complementary illumination relay systems with a common imaging lens and sensor in accordance with one aspect of the present design.

A general representation of an inspection system 800 with two illumination sources according to one aspect of the present design is presented in FIG. 8. In this configuration, two illumination sources and complementary illumination relay systems are arranged with a common imaging lens and sensor. The first source in the present example is used for bright field imaging and the second source is used for dark field imaging. An illumination source 810 may emit, for example, light energy or flux and the imaging system may direct the bright field light energy towards a channel one illumination relay 815 (i.e. channel one illumination and imaging lens). The illumination relay 815 may comprise one or more reflective surfaces, a beam splitter, a reflector, a polarization lens, and/or an illumination and imaging lens relay arrangement, and any combinations thereof configured in a desirable manner.

Channel one illumination relay 815 may collect light energy emitted from the illumination source 810 and may project channel one light energy downward in a desirable manner onto inspected object 130 at field one 830 sufficient for detection by sensor 170 (not shown in FIG. 8). The present design may transfer the light energy that reflects off of inspected object 130 (i.e. specimen under inspection) to an image relay component 815. Another image relay component 855 may collect the reflected light energy and may transfer or project along image path 805 the reflected bright field light energy toward a split readout TDI or dual linear sensor. Sensor 170 outputs the detected bright field image information via a plurality of readout circuits at point 850. Such a system construction is well suited for use with TDI sensor 700.

In addition, a second illumination source (not shown) emits light energy or flux and may direct the light energy toward a channel two illumination relay 820 (i.e. channel two illumination and imaging lens). The illumination relay 820 may comprise one or more reflective surfaces, a beam splitter, a reflector, a polarization lens, and/or an illumination and imaging lens relay arrangement. Channel two illumination relay 820 collects the light energy emitted from the second illumination source and projects channel two light energy in a desirable manner onto inspected object 130 at field two 840 sufficient for detection by sensor 170. In this configuration, the imaging lens arrangement does not collect the light energy that reflects at point 895 off of inspected object 130 (i.e. specimen under inspection) at field 840. The image relay 855 collects the dark field light energy that scatters 898 off of inspected object 130 due to the illumination.

The image relay 855 collects the scattered light 898 and transfers or projects the received dark field light energy incident toward a TDI sensor operating in a split mode arrangement, or a dual linear sensor simultaneously with the bright field imaging mode. The sensor (not shown) outputs the detected dark field imaging mode information via a plurality of readout circuits. In this configuration, the present design affords simultaneous light exposure of the inspected object 130 and provides the bright field response as image data at point 850 and the dark field response as image data at point 860.

The present design illuminates the inspected object 130 using two different light sources and moves the object in a scanning direction 890 relative to the sensor. The output image data for the bright field moves in a direction 850 opposite in orientation to the object scan direction 890. In a similar manner, the output image data for the dark field channel moves in direction 860 resulting from the mirror/reflective surface discussed above with reference to FIGS. 4 and 5.

The field separation at the inspected object 130 between bright field illumination 830 and dark field illumination 840 may allow separate filtering or additional optical processing to be performed on each of these field regions within the image relay system. Furthermore, a separate image mode relay and mirroring arrangement may map the images onto one or more sensor arrays and may control the scan direction 890 of the two regions independently. Although this aspect describes use of a bright field and a dark field imaging mode, it should be well understood by one skilled in the art that this aspect may support a variety of optical imaging modes.

Figure 9:
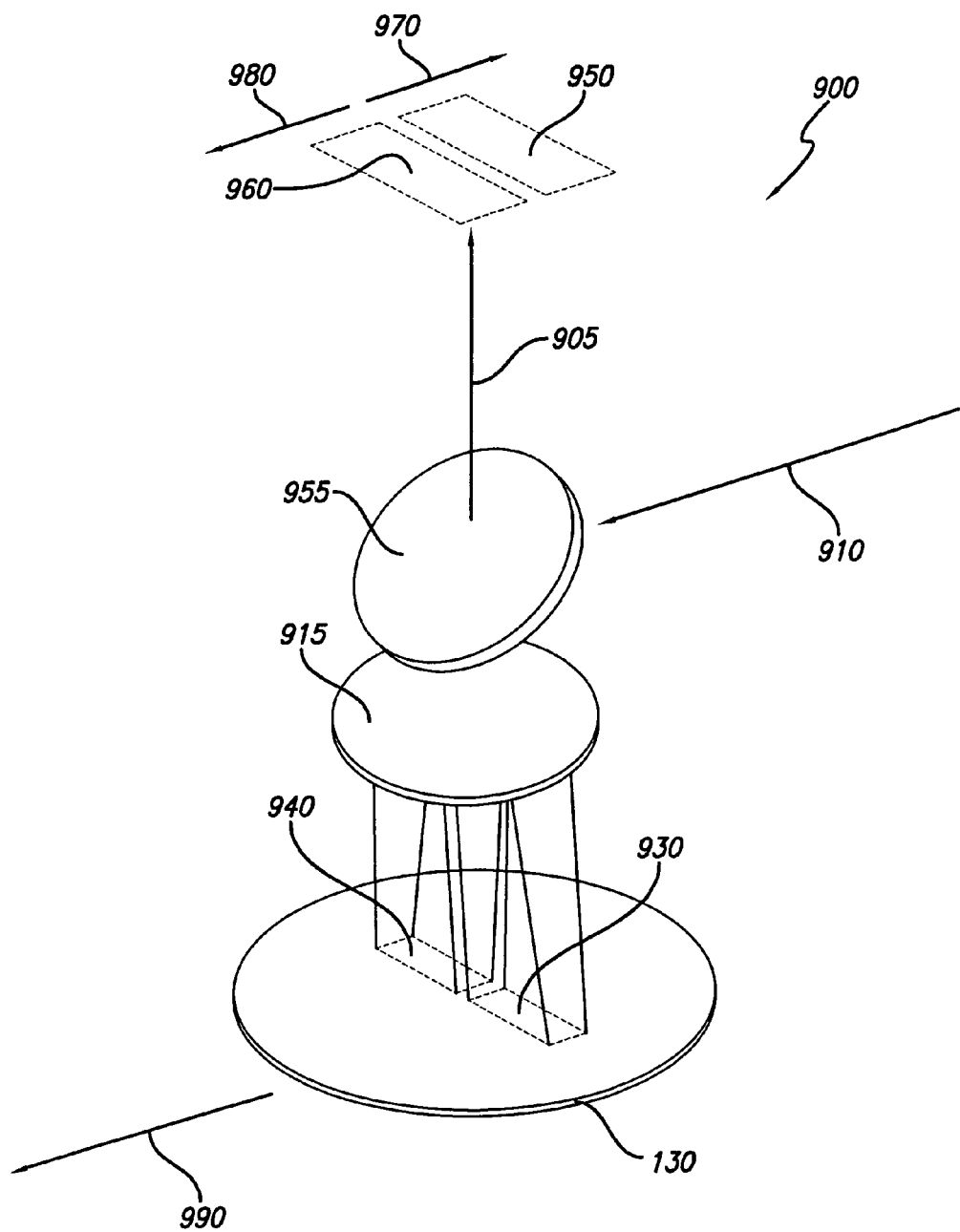
FIG. 9 is a general representation of an inspection system configured to simultaneously scan two non-overlapping regions of the object and imaged onto a sensor in accordance with a second aspect of the present design.

A general representation of an inspection system 900 suitable for simultaneously imaging two non-overlapping field regions of inspected object 130 according to a second aspect of the present design is presented in FIG. 9. In this configuration, a single illumination source and illumination relay system are arranged with a common imaging lens and sensor. An illumination source 910 emits bright field light energy or flux and directs the bright field light energy towards a channel one illumination relay 915 (i.e. channel one illumination and imaging lens). The channel one illumination relay 915 comprises one or more reflective surfaces, a beam splitter, a reflector, a polarization lens, and an illumination and imaging lens relay arrangement, and any combinations thereof configured in a desirable manner. Channel one illumination relay 915 collects bright field light energy emitted from the illumination source 910 and projects bright field light energy downward in a desirable manner onto inspected object 130 at field one 930 and field two 940 sufficient for detection by sensor 170 (not shown in FIG. 9) while scanning the inspected object 130 in the direction indicated 990.

In the present design description the light energy that reflects off of inspected object 130 (i.e. specimen under inspection) from field one 930 and field two 940 is transmitted to an image relay 915. Image mode relay 915 collects the reflected light energy from these fields and transfers or projects along image path 905 received reflected bright field imaging information towards a bidirectional split readout TDI or dual linear sensor. The mirror arrangement comprising image mode relay 915, 955 may relay field one 930 reflected light energy incident on one sensor sub-region as field one image data 950 while simultaneously relaying field two 940 reflected light energy incident on a separate sensor sub-region as field two image data 960.

Sensor 170 (not shown in FIG. 9) outputs the detected image information response from field one image 950 and may generate signal output via a plurality of readout circuits in scanning direction 970. In a similar manner, the information response from field two image 960 may generate signal output via a plurality of readout circuits in scanning direction 980.

In this configuration, the present design makes efficient use of the full capabilities of each sub-array within the split mode TDI sensor and may afford an increase in throughput and faster inspected object 130 scans employing a single illumination source.

Figure 10:
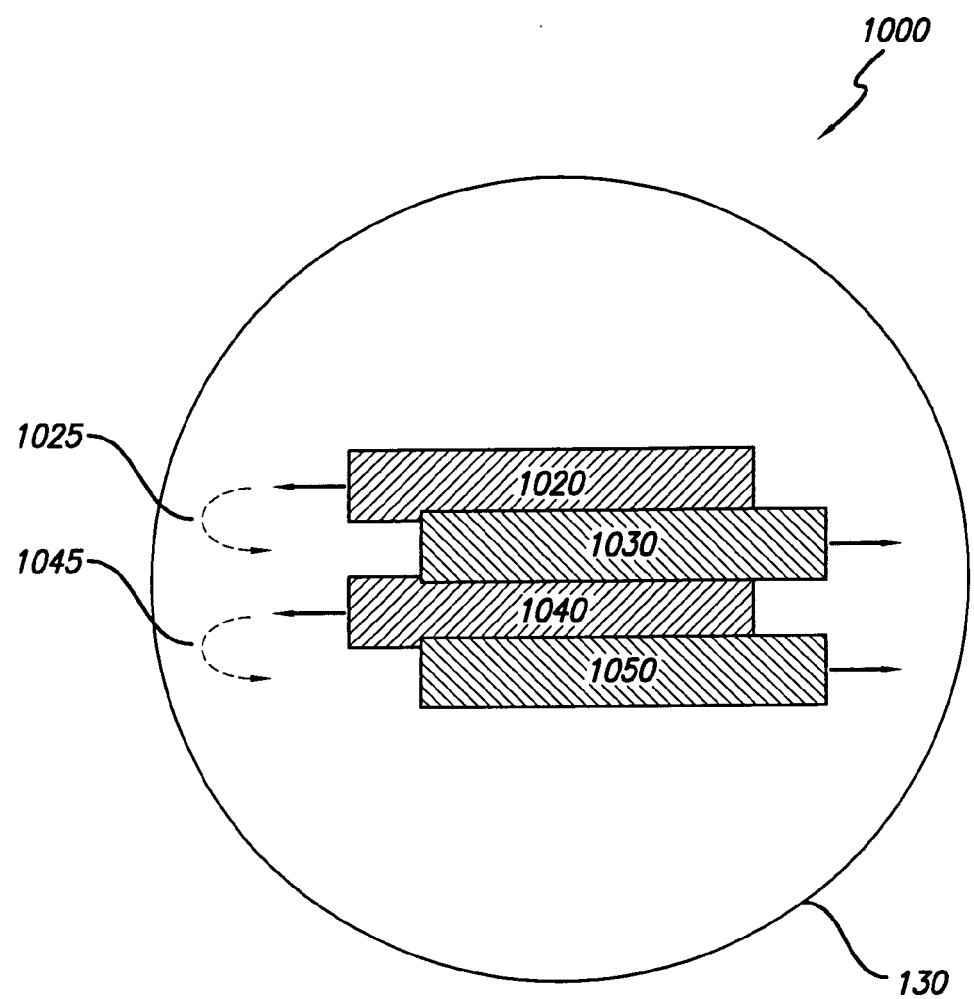
FIG. 10 is a conceptual diagram illustrating 100% inspection of an object using two non-overlapping fields in accordance with the second aspect of the present design.

A further aspect of the present design provides an inspection method 1000 for achieving 100% inspection of an object using two non-overlapping fields and spatially interleaved scans in accordance with the second aspect of the present design. FIG. 10 illustrates inspection method 1000 and a special scanning arrangement sufficient to performing 100% inspection of the inspected object 130 in an efficient manner. The method initiates a first pass scan from right to left, of inspected object 130 and may simultaneously perform a scan one of field one 1020 and of field two 1040. When the right to left scan reaches the edge of inspected object 130, the scanning shifts vertically and changes to the opposite direction and initiates a second pass scan from right to left of inspected object 130.

Inspection method 1000 may provide a mechanism to adjust the gaps located between fields. This mechanism ensures that the gap between fields remains slightly less than the height of each field. The second pass scan performs a simultaneous scan of field one 1030 and field two 1050. The shift and change in scanning direction occurs at point 1025 for field one and at point 1045 for field two. When the second pass scan completes, the scanning shifts back to the original, or first pass, scanning direction and may perform a plurality of repeating spatially interleaved scan passes (i.e. scan three, scan four, etc.) providing overlap of imaged regions and sufficient to cover the entire inspected object 130. Inspection method 1000 may perform an efficient inspection of 100 percent of the inspected object with minimal overlapping.

Figure 11:
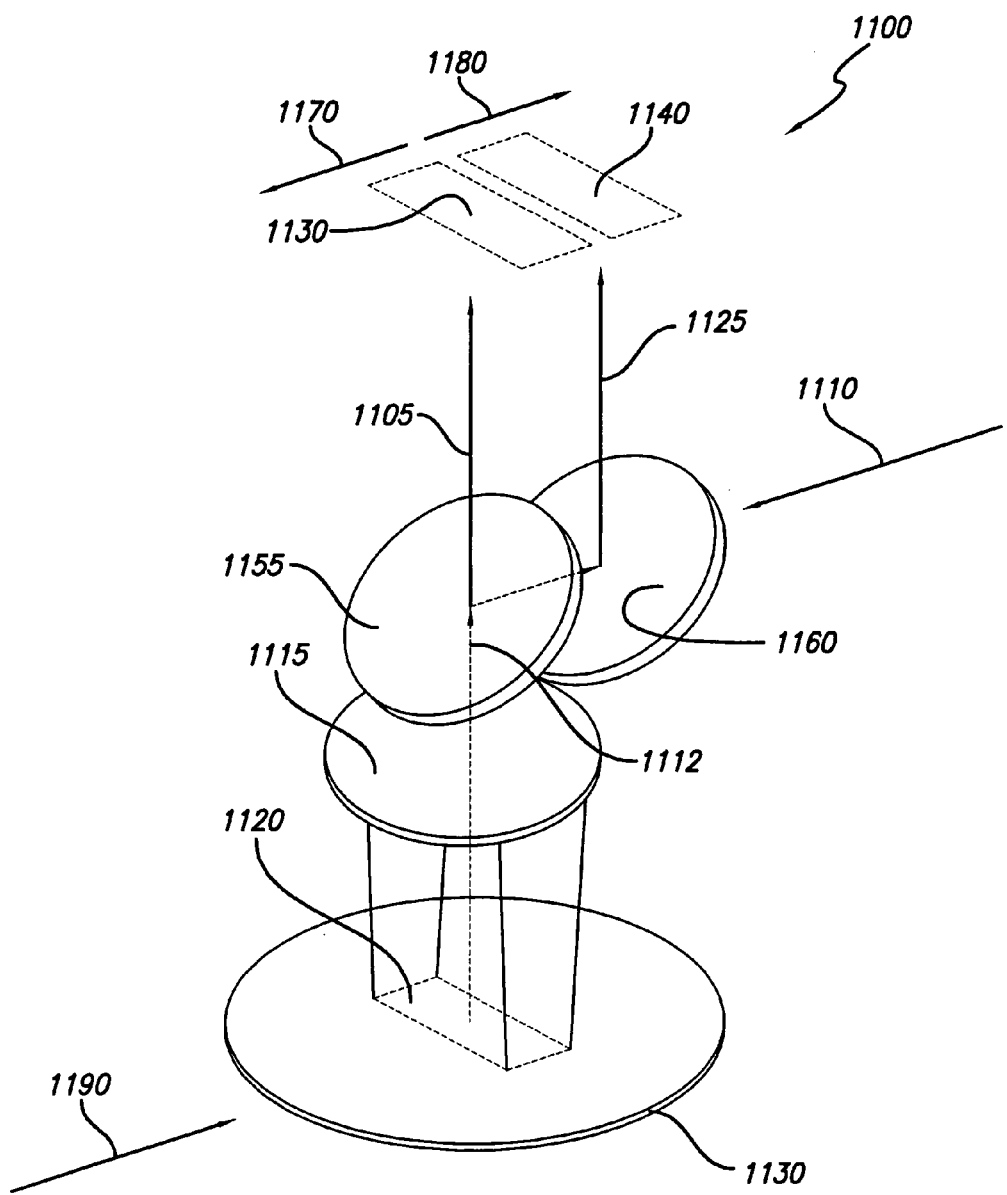
FIG. 11 is a general representation of an inspection system configured with one illumination source and two image relays, a common imaging lens, and a sensor to yield two illumination modes in accordance with a third aspect of the present design.

A general representation of an inspection system 1100 for projecting one illumination source onto an inspected object 130, and collecting two different imaging modes from the reflected light energy at the same time according to a third aspect of the present design is presented in FIG. 11. In this configuration, the inspection system 1100 comprises a single illumination source (not shown) and an arrangement for two complementary image mode relay components with a common imaging lens and sensor collecting two different types of illumination. An illumination source emits light energy or flux and directs the light energy along path 1110. Illumination relay 1115 may comprise one or more reflective surfaces, a beam splitter, a reflector, a polarization lens, and/or an illumination and imaging lens relay arrangement, and any combinations thereof. Illumination relay 1115 may collect light energy emitted from the illumination source and may project the light energy downward in a desirable manner onto inspected object 130 at field location 1120 sufficient for detection by sensor 170 (not shown in FIG. 11) while scanning the inspected object 130 in the direction 1190.

The present design transmits the light energy that reflects off of inspected object 130 (i.e. specimen under inspection) from field location 1120 to image relay 1155. Image relay 1155 collects the reflected light energy from field location 1120 and transfers or projects along path 1105 received reflected imaging information towards a bidirectional split readout TDI or dual linear sensor. The mirror arrangement comprising image relay 1155 may relay field location 1120 image mode one along path 1105 to the first sensor sub-region as field image data 1130. In addition, image relay 1155 may separate the reflected light energy by splitting the image near the system's pupil plane 1155. Splitting the image may comprise separating different types of illumination or imaging modes. Image relay 1155 transfers the second image light energy, to image relay 1160. Image relay 1160 collects the reflected light energy from field location 1120 and transfers or projects along path 1125 received reflected imaging information towards a bidirectional split readout TDI or dual linear sensor. The mirror arrangement comprising image relay 1160 relays field location 1120 image mode two along image path 1125 to the second sensor sub-region as field one image data 1140.

Sensor 170 (not shown) outputs the detected image information from field location 1120 image mode one 1130 and generates signal output via a plurality of readout circuits in scanning direction 1170. In a similar manner, a different image response is received from field location 1120 using image mode two 1140 and generates signal output via a plurality of readout circuits (not shown in FIG. 11) in scanning direction 1180.

In this configuration, the present design may simultaneously acquire two images from the same field location 1120 and process each image separately or in combination at sensor 170. The inspection system 1100 may be configured to simultaneously collect images using modes including but not limited to: large-signal/small-signal readout, multi-spectral imaging, transmitted/reflected simultaneous imaging, and broadband/narrow band optical imaging modes. Inspection system 1100 may employ common optic components for the imaging relay and imaging mode relays in a manner wherein the relative alignment and focus are correlated, and general stability of the two images is significantly improved over using separate optical components or sensors. In this embodiment, image information from the same object location may be split at or near the pupil of the imaging system to highlight or to de-emphasize certain features in each channel.

One embodiment of the design of FIG. 11 may include a narrow band illumination channel where the narrow band illumination is derived from the broadband illumination source. For example, a mercury xenon lamp may be employed as the illumination source, and image relay 1160 may use i-line wavelength light for the narrow band illumination and the remaining suitably filtered lamp output to form the broadband illumination. Image relay 1160 in such a scenario may comprise a narrow band reflective surface, where the narrow band light energy is used as one inspection channel and broadband light energy for the other channel via image relay 1155. Other forms of illumination splitting may be employed.

Figure 12:
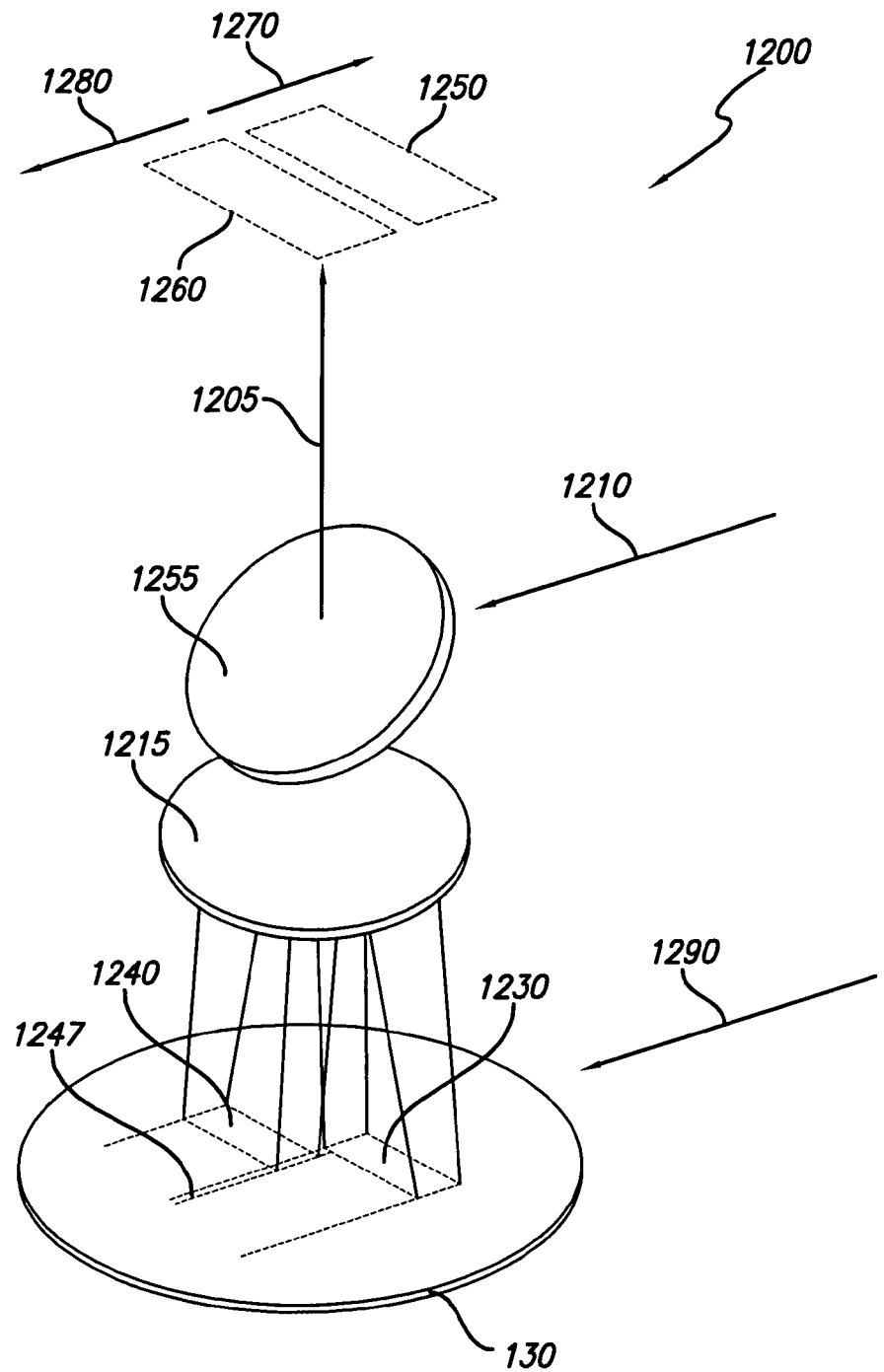
FIG. 12 is a general representation of an inspection system configured to simultaneously scan two non-overlapping field regions of the object and imaged onto a sensor in accordance with a fourth aspect of the present design.

A general representation of an inspection system 1200 suitable for simultaneously imaging two non-overlapping field regions of inspected object 130 according to a fourth aspect of the present design is presented in FIG. 12. In this configuration, an illumination source and complementary illumination relay system are arranged with a common imaging lens and sensor. The illumination source 1210 emits light energy or flux and directs the light energy towards an illumination relay 1255, 1215. The illumination relay 1255, 1215 may comprise one or more reflective surfaces, a beam splitter, a reflector, a polarization lens, and an illumination and imaging lens relay arrangement, and any combinations thereof configured in a desirable manner. Illumination relay 1215 collects light energy emitted from the illumination source 1210 and may project light energy downward in a desirable manner onto inspected object 130 at field one 1230 and field two 1240 sufficient for detection by sensor 170 (not shown in FIG. 12) while scanning the inspected object 130 in the direction 1290.

The present design may transfer the light energy that reflects or scatters off of inspected object 130 (i.e. specimen under inspection) from field one 1230 and field two 1240 to an image relay 1215, 1255. Image relay 1255 may collect the reflected light energy from these fields and may transfer or project along imaging path 1205 received image information towards a bidirectional split readout TDI or dual linear sensor. The mirror arrangement comprising image relay 1255 relays field one 1230 reflected light energy incident on one sensor sub-region as field one image data 1250 while simultaneously relaying field two 1240 reflected light energy incident on a separate sensor sub-region as field two image data 1260. In this arrangement, the present design may produce a small overlap of inspected regions 1247, resulting from field one 1230 and field two 1240 covering the same region of inspected object 130 at different times.

Sensor 170 (not shown in FIG. 12) outputs the detected image information from field one image data 1250 and may generate signal output via a plurality of readout circuits in scanning direction 1270. In a similar manner, imaging mode information response from field two image data 1260 may generate signal output via a plurality of readout circuits (not shown in FIG. 12) in sensor scan direction 1280.

In this configuration, the field locations are not orthogonal to the scanning direction 1290 and the two inspected region images are relayed to a bidirectional TDI sensor operating in split readout mode capturing each image region. Inspection system 1200 eliminates any gap between scanned regions, thus achieving 100 percent inspection of the specimen. The scan time difference introduced between the two image field regions 1230 and 1240 in this embodiment may be accounted for in the image processing system 105.

The foregoing is not determinative or exclusive or inclusive of all components, interfaces, communications, and operational modes employable within the present design. The design presented herein and the specific aspects illustrated are meant not to be limiting, but may include alternate components while still incorporating the teachings and benefits of the invention, namely a high-speed image forming system, sensor, and acquisition system to simultaneously collect multiple images or "channels" enabling semiconductor integrated circuit manufactures to meet the full range of inspection requirements for transmitting and reflecting specimens in a time and cost efficient manner. While the invention has thus been described in connection with specific aspects thereof, it will be understood that the invention is capable of further modifications. This application is intended to cover any variations, uses or adaptations of the invention following, in general, the principles of the invention, and including such departures from the present disclosure as come within known and customary practice within the art to which the invention pertains.

What is claimed is:

1. A method for a dual channel inspection of at least one region of a specimen, comprising:
   receiving incident light energy from the at least one region of the specimen, wherein said receiving comprises receiving a plurality of channels of light energy;
   reorienting at least one channel of light energy relative to one other channel of light energy; and
   simultaneously providing the reoriented channel of light energy and the one other channel of light energy to a sensor.

2. The method of claim 1, further comprising simultaneously transmitting data representing the reoriented channel of light energy and the other channel of light energy from the sensor subsequent to said simultaneously providing.

3. The method of claim 1, wherein the sensor comprises a time delay and integration (TDI) sensor.

4. The method of claim 1, wherein said reorienting comprises transmitting the at least one channel of light energy to at least one first reflective surface and transmitting the other channel of light energy to at least one second reflective surface.

5. The method of claim 2, wherein said reorienting enables scanning the specimen in a first direction to yield light energy passing in a first direction on one portion of the sensor and light energy passing in a second direction on a second portion of the sensor.

6. The method of claim 1, wherein the receiving incident light energy comprises receiving incident light energy from one region of the specimen as one channel and receiving light energy from a second region of the specimen as a second channel.

7. The method of claim 1, wherein the receiving incident light energy comprises receiving light energy having one characteristic from one region as one channel and receiving light energy having another characteristic from the one region as a second channel.

8. The method of claim 7, wherein the one characteristic comprises brightfield energy and the second characteristic comprises darkfield energy.

9. The method of claim 1, wherein the receiving incident light energy comprises receiving light energy having one characteristic from one region as one channel and receiving light energy having another characteristic from another region as a second channel.

10. A sensor configured to receive light energy for purposes of inspecting a specimen, comprising:
    a first sensing region configured to receive a first channel of image data from the specimen, wherein the first channel of image data corresponds to a first channel of data received from the specimen;
    a second sensing region configured to receive a second channel of image data from the specimen, wherein the second channel of image data corresponds to a reoriented second channel of data received from the specimen;
    first readout circuitry connected to the first region configured to read the first channel of image data from the sensor; and
    second readout circuitry connected to the second region configured to read the second channel of image data from the sensor simultaneous with reading the first channel of image data from the sensor.

11. The sensor of claim 10, wherein the first sensing region comprises a line.

12. The sensor of claim 11, wherein the second sensing region comprises a line.

13. The sensor of claim 10, wherein the first channel of image data is received in one orientation from the specimen and the second channel of image data is received in a rotated orientation from the specimen.

14. The sensor of claim 13, wherein data reorientation causes data to progress from inner portions of the first sending region and second sensing region to outer portions of the first sensing region and second sensing region when the specimen is scanned in one direction.

15. A system for performing a simultaneous dual channel inspection of a specimen, comprising:
    at least one illuminator configured to provide light energy to the specimen;
    orientation optics configured to receive two channels of light energy from the specimen and reorient one channel of light energy, thereby configured to provide a reoriented channel of light energy and a nonreoriented channel of light energy; and a sensor configured to receive and simultaneously process the reoriented channel of light energy and the nonreoriented channel of light energy.

16. The system of claim 15, wherein the orientation optics comprise: at least one lens; and at least one reflective surface.

17. The system of claim 16, further comprising a set of insertable reflective surfaces configured to provide an alternate path for reorienting images formed on the sensor.

18. The system of claim 15, wherein the sensor comprises a time delay and integration (TDI) sensor configured to receive data and simultaneously provide data from one region of the sensor via first readout circuitry and data from a second region of the sensor via second readout circuitry.

19. The system of claim 15, wherein said orienting optics are configured to enable scanning the specimen in a first direction to yield light energy passing in a first direction on one portion of the sensor and light energy passing in a second direction on a second portion of the sensor.

20. The system of claim 15, wherein the at least one illuminator comprises a brightfield illuminator and a darkfield illuminator and the two channels of light energy received from the specimen comprise a channel of brightfield light energy and a channel of darkfield light energy.

21. The system of claim 15, further comprising an optical element between the at least one element and the specimen configured to provide light energy having one characteristic to the specimen and light energy having a second characteristic to the specimen.

22. The system of claim 21, wherein the first characteristic comprises a first wavelength and the second characteristic comprises a second wavelength.

23. The system of claim 21, wherein the first characteristic comprises a first polarization and the second characteristic comprises a second polarization.

24. The system of claim 10, wherein said first sensing region differs in size from said sensing region wherein different sized regions enhance dynamic range and sensitivity control.

25. The system of claim 10, wherein said fist sensing region is substantially identical in size to said second sensing region.

26. The system of claim 15, wherein the at least one illuminator comprises a narrow band illuminator and a broadband illuminator.

27. The system of claim 15, wherein the at least one illuminator comprises a narrow band illuminator, and further wherein the orientation optics comprise filtering optics configured to filter narrow band illumination from said narrow band illuminator into broadband illumination.

28. The system of claim 27, wherein said narrow band illuminator comprises a mercury xenon lamp and wherein the orientation optics split i-line wavelength energy from the mercury xenon lamp using at least one narrow band reflective surface.

* * * * *